United States Patent
Wu et al.

(10) Patent No.: US 10,758,178 B2
(45) Date of Patent: Sep. 1, 2020

(54) MEASURING METHOD OF HUMAN BODY

(71) Applicant: HTC Corporation, Taoyuan (TW)

(72) Inventors: Chun-Yih Wu, Taoyuan (TW);
Ta-Chun Pu, Taoyuan (TW);
Yen-Liang Kuo, Taoyuan (TW)

(73) Assignee: HTC Corporation, Taoyuan (TW)

( * ) Notice: Subject to any disclaimer, the term of this patent is extended or adjusted under 35 U.S.C. 154(b) by 50 days.

(21) Appl. No.: 16/214,125

(22) Filed: Dec. 9, 2018

(65) Prior Publication Data

US 2019/0104988 A1 Apr. 11, 2019

Related U.S. Application Data

(62) Division of application No. 14/875,679, filed on Oct. 5, 2015, now Pat. No. 10,182,758.

(51) Int. Cl.
*A61B 5/00* (2006.01)
*A61B 5/107* (2006.01)

(52) U.S. Cl.
CPC .......... *A61B 5/4872* (2013.01); *A61B 5/0064* (2013.01); *A61B 5/1075* (2013.01)

(58) Field of Classification Search
CPC ............................. A61B 5/0064; A61B 5/4872
See application file for complete search history.

(56) References Cited

U.S. PATENT DOCUMENTS 9,289,158 B2* 3/2016 Pfeiffer ................. A61B 5/0064
10,182,758 B2* 1/2019 Wu ....................... A61B 5/4872
2005/0101884 A1 5/2005 Weeks et al.
2007/0293752 A1* 12/2007 Simpkin .............. A61B 5/1077
600/407
2011/0317890 A1 12/2011 Baroni et al.

FOREIGN PATENT DOCUMENTS

CN 103126681 6/2013

OTHER PUBLICATIONS

"Office Action of China Counterpart Application," dated Feb. 2, 2019, p. 1-p. 12.
"Office Action of China Counterpart Application," dated Sep. 24, 2019, p. 1-p. 16.

* cited by examiner

*Primary Examiner* — Eric D. Bertram
(74) *Attorney, Agent, or Firm* — JCIPRNET

(57) ABSTRACT

A measuring device, including a device body, distance measuring units, optical measuring units and a processing unit, is provided. The device body includes a sensing reference surface adapted for a person to be measured to stand thereupon. The optical measuring units are disposed corresponding to the respective distance measuring units. Each of the distance measuring units transmits distance measuring signals to body areas of the person, so as to obtain distance information between each of the distance measuring units and the body areas of the person. Each of the optical measuring signal transmits measuring light to the person to be measured, and receives a measuring pattern formed through reflection of the measuring light from the person. The processing unit calculates and reconstructs a three-dimensional surface structure of the body areas of the person according to the respective distance information obtained from the distance measuring units and the corresponding measuring patterns.

9 Claims, 6 Drawing Sheets

MEASURING METHOD OF HUMAN BODY

CROSS REFERENCE TO RELATED APPLICATION

This application is a divisional application of and claims the priority benefit of U.S. application Ser. No. 14/875,679, filed on Oct. 5, 2015, now U.S. Pat. No. 10,182,758. The entirety of the above-mentioned patent application is hereby incorporated by herein and made a part of specification.

BACKGROUND OF THE INVENTION

1. Field of the Invention

The invention relates to a measuring device, and particularly relates to a measuring device of a human body and a measuring method thereof.

2. Description of Related Art

Through the progress of civilization, various modern plagues caused by living or eating habits become an inevitable issue of modern people. Thus, diet and self-body control have become issues that people nowadays need to pay attention to. Human body measuring devices, such as body weight scales and body fat scales, are thus broadly used in our daily lives to allow people to constantly keep track of changes of their bodies.

However, to constantly keep track of the changes, the users prefer to use devices that can be operated in a household environment, so as to follow up the changes on daily basis without interruption. However, the measuring capability of the conventional human body measuring devices suitable for the household environment is still not quite as desirable as expected. For example, the resistive body fat scale that is commonly used in the household environment is only capable of measuring the body mass index (BMI) and the body fat percentage (BFP), and is limited in evaluating the actual composition of the body. Besides, even though the more specialized body volume index (BVI) measuring device is available for providing a precise body shape for a more precise analysis (especially the fat distribution in the abdominal region and the lower body), such device requires constant installation of structured light and a specific location, making the measuring platform too big to function as a household health product.

SUMMARY OF THE INVENTION

The invention provides a measuring device of a human body and a measuring method of a human body capable of reconstructing a user's body shape and structure to provide a body health evaluation result based on the body shape.

A measuring device according to an embodiment of the invention includes a device body, a plurality of distance measuring units, a plurality of optical measuring units and a processing unit. The device body includes a sensing reference surface suitable for a person to be measured to stand thereupon. The distance measuring units are disposed adjacent to the sensing reference surface. In addition, distances from the respective distance measuring units to a center of the sensing reference surface are equal, and distances between the respective distance sensing units are equal. The optical measuring units are disposed corresponding to the respective distance measuring units. The processing unit is coupled to the distance measuring units and the optical measuring units. Each of the distance measuring units transmits a plurality of distance measuring signals to a plurality of body areas of the person to be measured, so as to obtain distance information between the each of the distance measuring units and the body areas of the person to be measured. Each of the optical measuring signal transmits measuring light to the person to be measured, and receives a measuring pattern formed through reflection of the measuring light from the person. The processing unit obtains the respective distance information from the respective distance measuring units and obtains the measuring patterns from the respective optical measuring units corresponding to the respective distance measuring units, and the processing unit calculates and reconstructs a three-dimensional surface structure corresponding to the body areas of the person to be measured based on the respective distance information obtained by the respective distance measuring units and the corresponding measuring patterns.

An embodiment of the invention provides a measuring method of a human body, suitable for measuring a person to be measured standing on a sensing reference surface of a measuring device of a human body. The measuring method of the human body includes steps as follows. First of all, a plurality of distance measuring signals are transmitted to a plurality of body areas of the person to be measured, so as to obtain distance information of the body areas of the person to be measured. Measuring light respectively corresponding to the measuring signals is transmitted to the person to be measured and a plurality of measuring patterns formed through reflection of the measuring light from the person to be measured are received. Then, the distance information and the measuring patterns respectively corresponding the distance information are obtained. Furthermore, a three-dimensional surface structure corresponding to the body areas of the person to be measured is calculated and reconstructed based on the respective distance information and the measuring patterns corresponding to the distance information.

Based on above, the embodiments of the invention provide the measuring device of the human body and the measuring method of the human body capable of reconstructing the three-dimensional body shape structure of the respective body areas of the person to be measured by using the distance to the person to be measured obtained using the distance measuring units and measuring the body shape using the optical measuring units.

In order to make the aforementioned and other features and advantages of the invention comprehensible, several exemplary embodiments accompanied with figures are described in detail below.

DESCRIPTION OF THE EMBODIMENTS

When using a conventional measuring device capable of providing a body volume index (BVI), light, such as a laser beam, is projected from a light source to a person to be measured to analyze a deformation rate of the light on the person to be measured, so as to obtain a structure of a body shape of the person to be measured. Since parameters such as a distance from the person to be measured to the light source and a projection angle of the light source must remain the same, such measurement requires the person to be measured to stand at a fixed position away from structured light. Thus, the measuring device providing BVI requires a large space, and is not suitable to be disassembled frequently. Thus, the invention provides a measuring device of a human body that adopts a simpler method to offer a capability of evaluating a body structure of a person to be measured. Thus, the user (i.e., the person to be measured) is able to obtain reconstructed information of the body in addition to measurements of body weight and body fat percentage in a household environment or by using a portable device, so as to obtain more accurate results of evaluation on the body and health. In the following, the technical solution and the embodiments of the invention are described in details.

Figure 1:
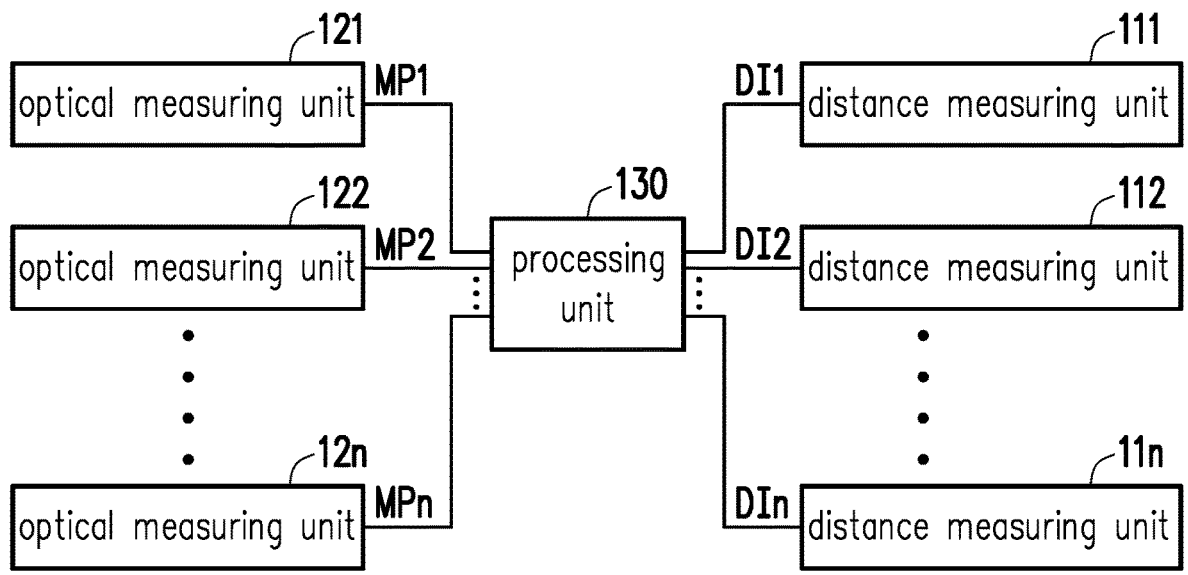
FIG. 1 is a block view illustrating a measuring device of a human body according to an embodiment of the invention.

FIG. 1 is a block view illustrating a measuring device of a human body according to an embodiment of the invention. Referring to FIG. 1, a measuring device 10 of a human body includes distance measuring units 111 to 11$n$, optical measuring units 121 to 12$n$, and a processing unit 130. The distance measuring units, the optical measuring units, and the processing unit are all disposed in a device body of the measuring device 10 of the human body. The device body includes a sensing reference surface suitable for the person to be measured to stand thereupon. The processing unit 130 may be a central processing unit disposed in the device body and has a capability of processing various signals received from the distance measuring units 111 to 11$n$ and the optical measuring units 121 to 12$n$.

The distance measuring units 111 to 11$n$ are disposed adjacent to the sensing reference surface. In addition, distances (e.g., a distance r) from the respective distance measuring units 111 to 11$n$ to a center of the sensing reference surface are substantially equal, and distances between the respective distance measuring units are substantially equal. In other words, in this embodiment, the distance measuring units 111 to 11$n$ are disposed on a circle with the center of the sensing reference surface as the center of the circle and with r as radius of the circle. In addition, an included angle between each of the distance measuring units 111 to 11$n$ and the adjacent distance measuring unit (e.g., the distance measuring unit 111 and the adjacent distance measuring unit 112) is 360/$n$ degrees.

The optical measuring units 121 to 12$n$ are disposed in correspondence with the distance measuring units 111 to 11$n$. For example, the optical measuring unit 121 is disposed adjacent to the distance measuring unit 111 or perpendicular to the distance measuring unit 111, such that a distance from the optical measuring unit 121 to the center of the sensing reference surface is similar to the distance from the distance measuring unit 111 to the center of the reference sensing surface. The same setting applies to other distance measuring units and optical measuring units. The processing unit 130 is coupled to the distance measuring units 111 to 11$n$ and the optical measuring units 121 to 121$n$.

In this embodiment, from bottom to top, the body of the person to be measured is divided into a plurality of body areas. Each of the distance measuring units 111 to 11$n$ transmits a plurality of distance measuring signals to the body areas of the person to be measured, so as to obtain distance information DI1 to DI$n$ between the distance measuring units 111 to 11$n$ and the body areas of the person to be measured. Each of the optical measuring units 121 to 12$n$ transmits measuring light to the person to be measured and receives each of measuring patterns MP1 to MP$n$ formed through reflection of the measuring light from the person to be measured. The processing unit 130 obtains the distance information DI1 to DI$n$ from the respective distance measuring units 111 to 11$n$, and obtains the measuring patterns MP1 to MP$n$ from the respective optical measuring units 121 to 12$n$ disposed in correspondence with the distance measuring units 111 to 11$n$ respectively. The processing unit 130 calculates and reconstructs a three-dimensional surface structure corresponding to the body areas of the person to be measured based on the respective distance information DI1 to DI$n$ obtained by the respective distance measuring units 111 to 11$n$ and the corresponding measuring patterns MP1 to MP$n$.

Figure 2:
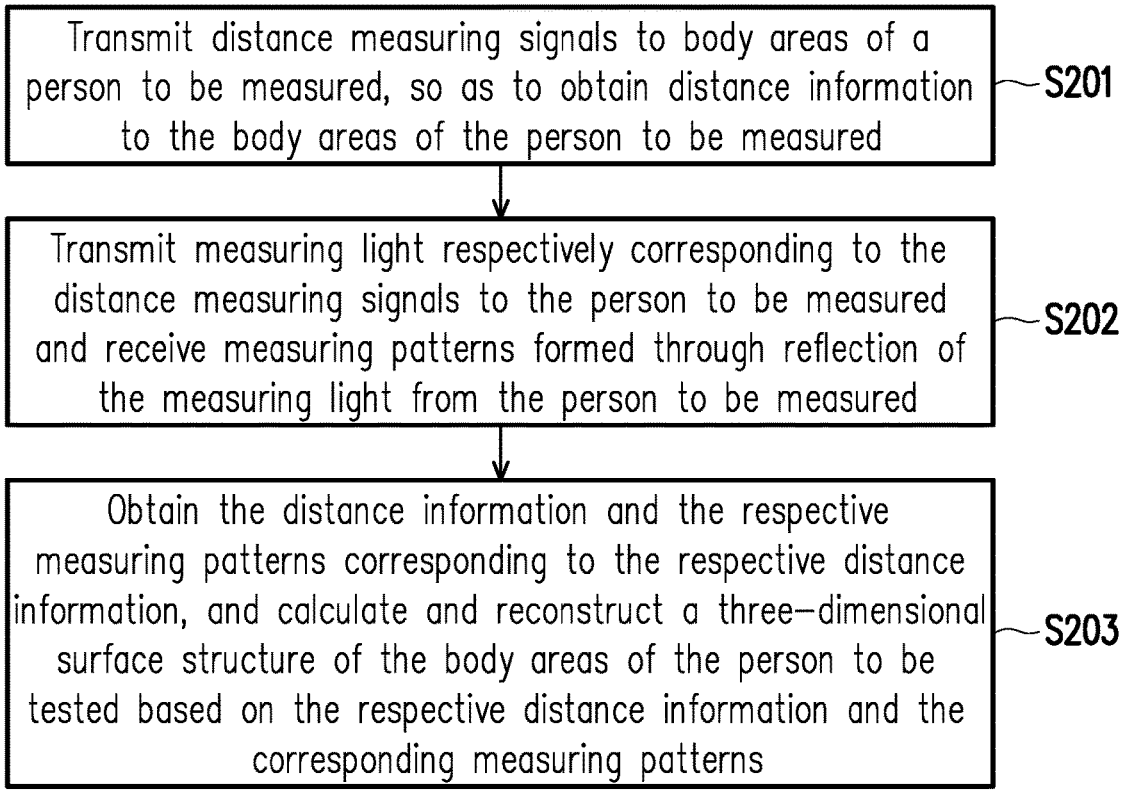
FIG. 2 is a flowchart illustrating a measuring method of a human body according to an embodiment of the invention.

FIG. 2 is a flowchart illustrating a measuring method of a human body according to an embodiment of the invention. Here, the measuring method of the human body is suitable for measuring the person to be measured standing on the measuring device of the human body. Referring to FIG. 2, first of all, the distance measuring signals are transmitted to the body areas of the person to be measured at Step S201, so as to obtain the distance information of the body areas of the person to be measured. Then, at Step S202, the measuring light that respectively corresponds to the distance measuring signals is transmitted to the person to be measured, and the measuring patterns formed through reflection of the measuring light from the person to be measured are received. Afterwards, at Step S203, the distance information and the measuring patterns respectively corresponding to the distance information are obtained, and the three-dimensional surface structure corresponding to the body areas of the person to be measured is calculated and reconstructed based on the respective distance information and the corresponding measuring patterns.

If only the measuring light transmitted by the optical measuring units 121 to 12$n$ and the measuring patterns MP1 to MP$n$ obtained through reflection are used, the processing unit 130 still needs distance information from the optical measuring units 121 to 12$n$ to the person to be measured, such as linear distances from the optical measuring units 121 to 12$n$ to the person to be measured or an included angle between the measuring light and the sensing reference surface, etc., to reconstruct the three-dimensional surface structure of the respective body areas by using information such as curvature changes of the measuring patterns MP1 to MP$n$ and identification of reference points. The requirement may be met by disposing the distance measuring units 111 to 11$n$ and returning the distance information DI1 to DI1 between the respective optical measuring units 121 to 12$n$ and the person to be measured.

Figure 3:
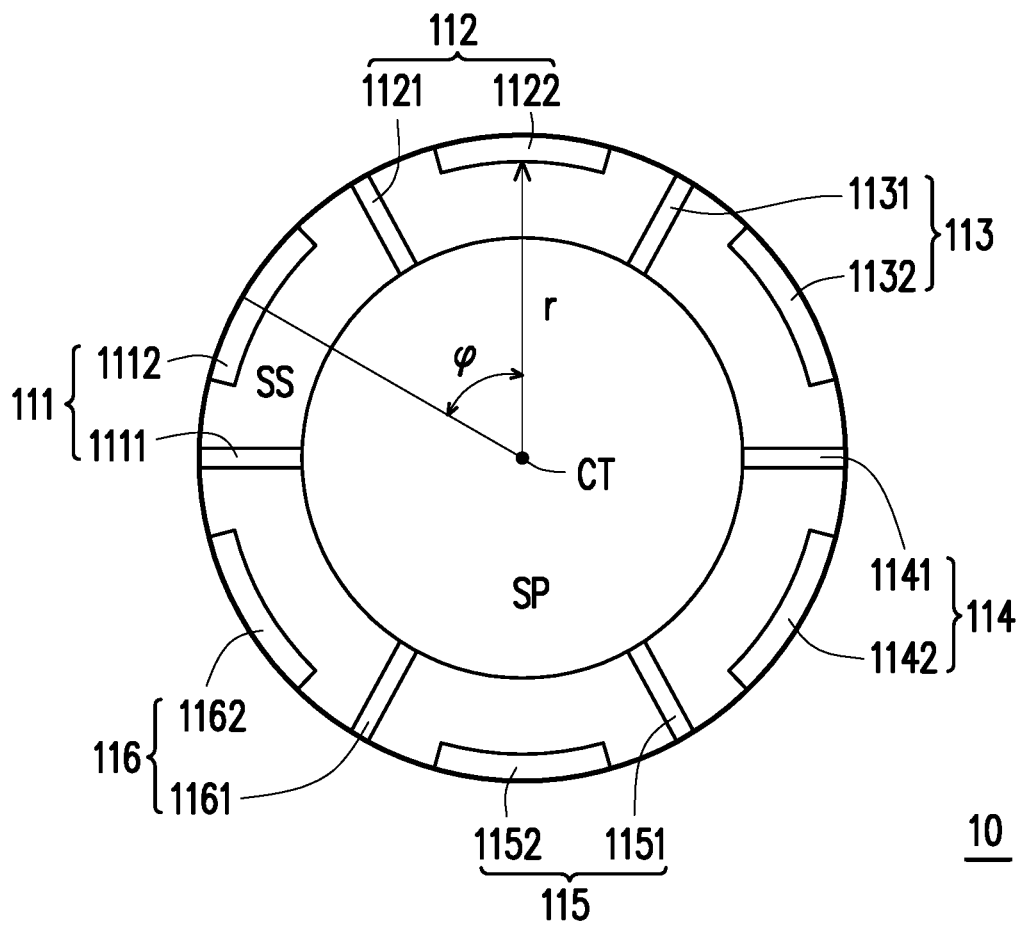
FIG. 3 is a schematic view illustrating an electronic device according to an embodiment of the invention.

In the following, implementation of the invention is described with the embodiments of the invention. FIG. 3 is a schematic view illustrating an electronic device according to an embodiment of the invention. Referring to FIG. 3, the device body of the electronic device 10 includes a sensing reference surface SP and a side edge SS. In this embodiment, it is set that the sensing reference surface SP is parallel to XY plane. Namely, FIG. 3 illustrates a top view toward a −Z-axis direction.

The sensing reference surface SP is circular and has a center CT. Also, the sensing reference surface SP is suitable for the person to be measured to stand thereupon. The side edge SS surrounds the sensing reference surface SP and has an included angle with respect to the sensing reference surface SP. In other words, from a side view (i.e., a side view toward a direction of XZ plane or a direction of ZY plane), the device body of the electronic device 10 is in a disc-like shape.

In this embodiment, the electronic device 10 includes six distance measuring units 111 to 116 and optical measuring units corresponding to the six distance measuring units 111 to 116 (i.e., n=6). The distance measuring units 111 to 116 and the optical measuring units are disposed on the side edge SS of the device body of the electronic device 10. Optical measuring units 121 to 126 and the distance measuring units 111 to 116 are disposed in a one-to-one relation. However, for the ease of illustration, only the distance measuring units 111 to 116 are shown in FIG. 3, while the optical measuring units 121 to 126 will be described in subsequent paragraphs. The six distance measuring units 111 to 116 are in an equi-distant arrangement. In other words, 360 degrees are evenly divided up by the six distance measuring units 111 to 116. Namely, an included angle between any two of the distance measuring units 111 to 116 is 60 degrees (i.e., an angle φ is equal to 60 degrees).

Continuing to refer to FIG. 3, each of the distance measuring units 111 to 116 includes one of multiple-frequency signal transmitters 1111, 1121, 1131, 1141, 1151, and 1161, one of multiple-frequency signal receivers 1112, 1122, 1132, 1142, 1152, and 1162, and a calculator. Taking the distance measuring unit 111 as an example, the multiple-frequency signal transmitter 1111 in the distance measuring unit 111 generates a plurality of distance measuring signals and transmits the distance measuring signals toward the respective body areas of the person to be measured.

Figure 4:
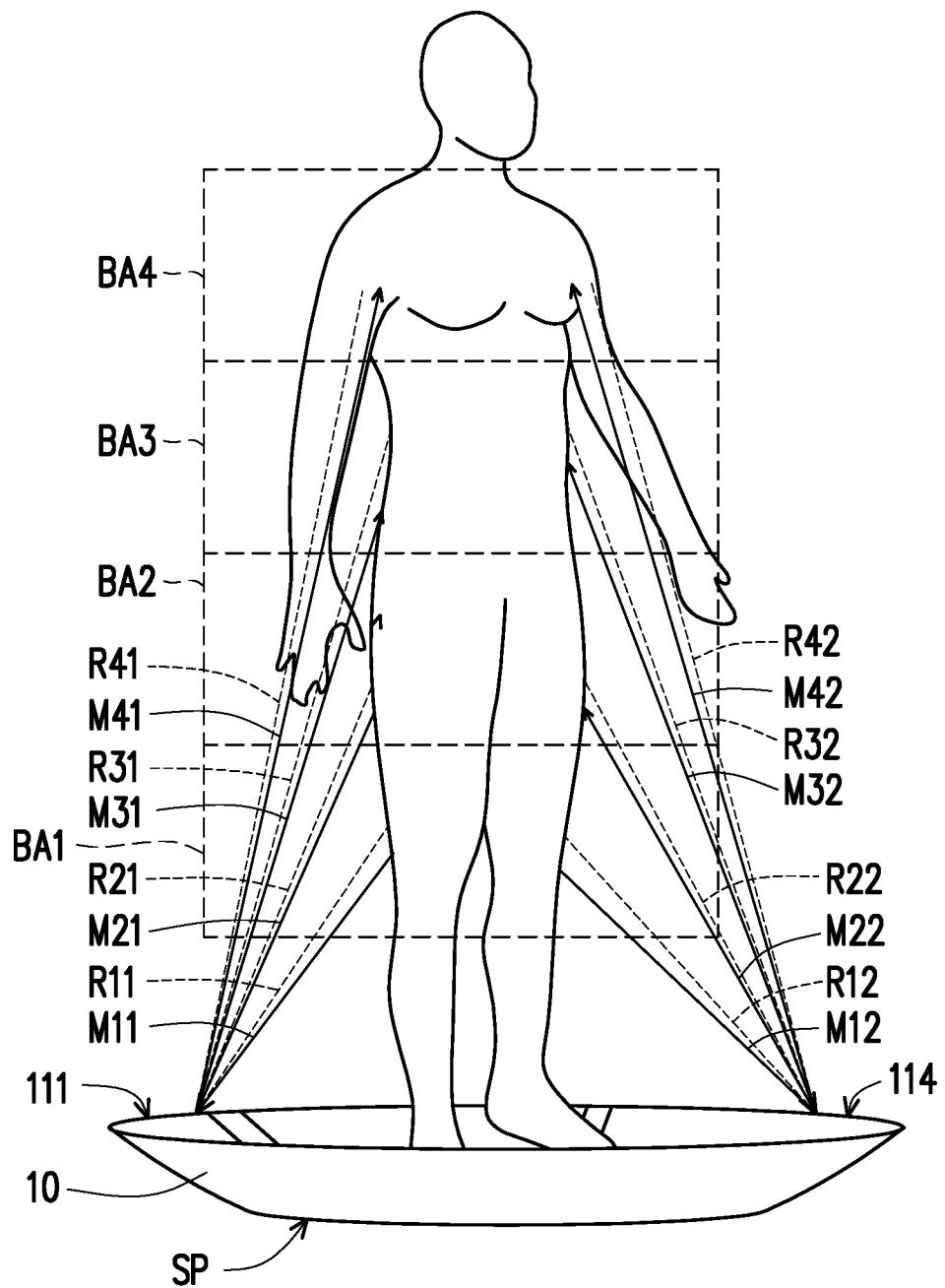
FIG. 4 is a schematic view illustrating a relation between the electronic device 10 according to the embodiment shown in FIG. 3 and body areas of the person to be measured.

FIG. 4 is a schematic view illustrating a relation between the electronic device 10 shown in FIG. 3 and the body areas of the person to be measured. Referring to FIGS. 3 and 4, in this embodiment, a whole body of the person to be measured may be divided into four body areas BA1 to BA4. The body areas BA1 to BA4 respectively correspond to areas of lower legs, upper legs, from buttocks to the lower abdomen, and from the upper abdomen to chest and upper arms of the person to be measured. It should be noted that the body areas BA1 to BA4 do not necessarily cover the whole human body, because areas of the head and feet which do not have a strong influence with shapes and fat distributions would not be taken into consideration. Accordingly, these areas are not evaluated in this embodiment.

However, the number of the body areas and the coverage of the body areas may be adjusted based on practical needs. For example, the processor 130 may adjust the sizes or number of the body areas, the number of the distance measuring signals, such as adjusting whether each of the distance measuring signals is turned on or not or modifying transmitting angles of the distance measuring signals based on data such as the height input by the user before the measurement or an input/measured body weight.

Figure 5:
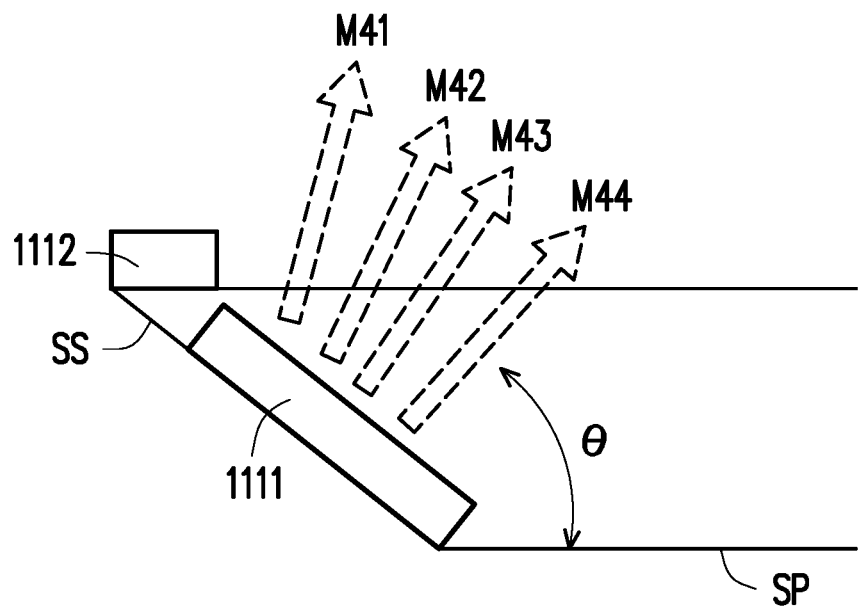
FIG. 5 is a schematic view illustrating an arrangement of a multiple-frequency signal transmitter and a multiple-frequency signal receiver of a distance measuring unit according to an embodiment of the invention.

In this embodiment, each of the distance measuring units 111 to 116 transmits four distance measuring signals to the body of a person to be measured PH. For example, the multiple-frequency signal transmitter 1111 of the distance measuring unit 111 transmits four distance measuring signals M11, M21, M31, and M41 to the body areas BA1 to BA4 of the person to be measured PH. FIG. 5 is a schematic view illustrating an arrangement of a multiple-frequency signal transmitter and a multiple-frequency signal receiver of a distance measuring unit according to an embodiment of the invention. Referring to FIG. 5, other than the top view shown in FIG. 3, FIG. 5 illustrates an arrangement between the multiple-frequency signal transmitter 1111 and the multiple-frequency signal receiver 1112 in the distance measuring unit 111 in a side view. Referring to FIG. 5, the multiple-frequency signal transmitter 1111 of the distance measuring unit 111 is disposed on the side edge SS of the device body of the electronic device 10, while the multiple-frequency signal receiver 1112 is similarly disposed on the side edge SS of the device body of the electronic device 10, but the position of the multiple-frequency signal receiver 1112 is slightly higher than the multiple-frequency signal transmitter 1111 and the multiple-frequency signal receiver 1112 does not overlap with the multiple-frequency signal transmitter 1111.

In addition, the multiple-frequency signal transmitter 1111 includes a transmitting antenna. In this embodiment, the transmitting antenna is a leaky wave antenna and has a frequency scanning capability. In addition, the transmitting antenna has different maximum radiation angles with respect to transmitting signals at different frequencies. For example, in this embodiment, the distance measuring signals M11, M21, M31, and M41 are radio-frequency signals having different central frequencies. The distance measuring signal M11 has the lowest central frequency and is transmitted toward a normal direction or a radiation surface (in this embodiment, the radiation surface of the antenna is parallel to the side edge SS) of the leaky wave antenna. The central frequencies of the distance measuring signals M21, M31, and M41 gradually increase, and maximum radiation angles thereof also gradually increase. For example, the central frequencies of the distance measuring signals M11, M21, M31, and M41 may be 60 GHz, 62 GHz, 64 GHz, and 68 GHz, respectively. However, the invention is not limited thereto.

The leaky wave antenna is configured as having an included angle θ between the radiation surface of the leaky wave antenna and the sensing reference surface SP. The person setting up the electronic device 10 may adjust the included angle θ to make the normal direction of the radiation surface of the leaky wave antenna toward the body area of the body areas of the person to be measured that is closest to the sensing reference surface SP, i.e., transmitting the distance measuring signal M11 toward the lowest body area of the body areas of the person to be measured, while the rest distance sensing signals M21, M31, and M41 are respectively transmitted toward other body areas. For example, the person setting up the electronic device 10 adjusts the included angle θ when setting up the electronic device 10, such that the distance measuring signal M11 is transmitted toward the body area BA1 of FIG. 4, while the distance measuring signals M21, M31, and M41 are respectively transmitted toward the body areas BA2, BA3, and BA4 shown in FIG. 4. The multiple-frequency signal transmitter 1111 may also include a component adjusting the included angle θ, and the included angle θ may be adjusted according to a control signal transmitted by the processor 130. The multiple-frequency signal receiver 1112 at least includes a frequency switcher and has a receiving antenna at least resonating in a frequency band. The multiple-frequency signal receiver 1112 may receive the distance measuring signals (e.g., reflected distance measuring signals R11, R21, R31, and R41 shown in FIG. 4) reflected from the person to be measured by using the frequency switcher and the receiving antenna.

Referring to FIGS. 3 and 4, in this embodiment, in order to prevent the multiple-frequency signal receivers of the distance measuring units 111 to 116 from interfering each other, the processing 130 controls the distance measuring units 111 to 116 to sequentially transmit the distance measuring signals (e.g., the multiple-frequency signal transmitter 1111 of the distance measuring unit 111 transmits at a time point t1, while the multiple-frequency signal transmitter 1121 of the distance measuring unit 112 transmits at the next time point t2, and so on so forth). Alternatively, in another embodiment of the invention, the processing unit 130 makes the distance measuring unit and another distance measuring unit facing the distance measuring unit transmit the distance measuring signals at the same time. For example, as shown in FIG. 4, when the distance measuring unit 111 transmits the distance measuring units M11, M21, M31, and M41, the distance measuring unit 114 at 180 degrees with respect to (i.e., facing) the distance measuring unit 111 transmits the distance measuring units M12, M22, M32, and M42 at the same time. However, the invention is not limited to such sequence arrangement of time.

The distance measuring signals respectively transmitted by the multiple-frequency signal transmitters 1111, 1121, 1131, 1141, 1151, and 1161 of the distance measuring units 111 to 116 are reflected by the respective body areas of the person to be measured. Also, the multiple-frequency signal receivers 1112, 1122, 1132, 1142, 1152, and 1162 of the distance measuring units 111 to 116 respectively receive the reflected distance measuring signals generated through reflection from the respective body areas of the person to be measured. For example, as shown in FIG. 4, the distance measuring signals M11, M21, M31, and M41 transmitted by the multiple-frequency signal transmitter 1111 of the distance measuring unit 111 are respectively reflected after arriving the body areas BA1 to BA4. The multiple-frequency signal receiver 1112 of the distance measuring unit 111 may then receive the reflected distance measuring signals R11, R21, R31, and R41 from the body areas BA1, BA2, BA3, and BA4. Similarly, other distance measuring units 112 to 116 may also receive the reflected distance measuring signals from the body areas BA1 to BA4 in a similar way. For example, the distance measuring unit 114 shown in FIG. 4 also receives reflected distance measuring signals R12, R22, R32, and R42 from the body areas BA1 to BA4 in a direction at 180 degrees with respect to the distance measuring unit 111.

The calculator of the distance measuring unit 111 is coupled to the multiple-frequency signal transmitter 1111 and the multiple-frequency signal receiver 1112, and may be disposed together with the multiple-frequency signal transmitter 1111 and the multiple-frequency signal receiver 1112. The calculator of the distance measuring unit 111 may make use of time of flight (TOF) to obtain the distance information between the distance measuring unit 111 and the respective body areas BA1 to BA4 of the person to be measured. More specifically, the calculator of the distance measuring unit 111 may calculate distance values between the distance measuring unit 111 and the body areas BA1 to BA4 based on corresponding round-trip time values including transmitting times that the multiple-frequency signal transmitter 1111 respectively transmits the distance measuring signals M11, M21, M31, and M41 and receiving times that the multiple-frequency signal receiver 1112 respectively receives the reflected distance measuring signals R11, R21, R31, and R41. The calculator of the distance measuring unit 111 may then integrate the distance values and other distance-related information (e.g., the current transmitting angle, etc.) to form the distance information DI1, and transmit the distance information DI1 to the processing unit 130. The calculators of the distance measuring units 112 to 116 may also respectively obtain the distance information DI2 to DI6 in a similar way. In addition, the distance information DI2 to DI6 also respectively include distance values from the distance measuring units 112 to 116 and the body areas BA1 to BA4. In addition, the distance information (e.g., the distance information DI1 to DI6) may include the distance values from the distance measuring unit 111 to the body areas BA1 to BA4, or simply include an absolute distance to the person to be measured at a specific elevation angle (i.e., an included angle between the distance measuring signal and the XY plane, such as an angle corresponding to the included angle θ shown in FIG. 5) obtained through conversion based on the distance values. However, the invention is not limited thereto.

Then, the processing unit 130 of the electronic device 10 may obtain the distance information DI1 to DI6 from the calculators of the respective distance measuring units 111 to 116. Thus, the processing unit of the electronic device 10 obtains the distance information at six angles (corresponding to the included angle φ shown in FIG. 3) in the front, back, left, and right of the person to be measured. Accordingly, the processing unit 130 of the electronic device 10 may perform calculation by using a triangulation method, for example, or other suitable methods, to obtain the absolute distances between the distance measuring units 111 to 116 and the person to be measured, including absolute distances from the XY plane and the absolute distances to the person to be measured at least one specific elevation angle. Here, by using the information provided by the optical measuring units together, the processing unit 130 is able to obtain a continuous variation of the body shape of the person to be measured on Z-axis, so as to reconstruct and obtain the three-dimensional surface structure of the respective body areas of the person to be measured.

Figure 6:
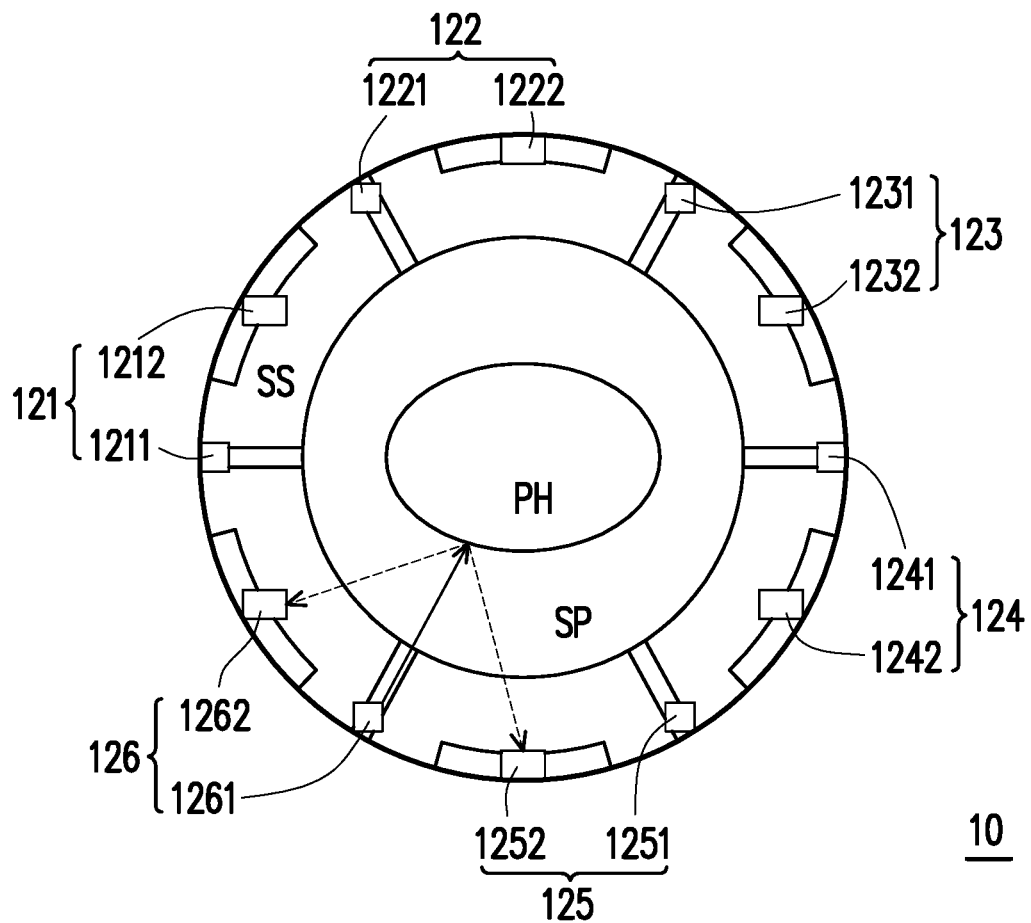
FIG. 6 is a schematic view illustrating an arrangement of an optical measuring unit of an electronic device according to the embodiment shown in FIG. 3.

FIG. 6 is a schematic view illustrating an arrangement of an optical measuring unit of an electronic device according to the embodiment shown in FIG. 3. Referring to FIG. 3 and FIG. 6, in this embodiment, the optical measuring units 121 to 126 are all disposed in correspondence with the distance measuring units 111 to 116. For example, the optical measuring unit 121 includes an optical transmitter 1211 and an optical image sensor 1212. The optical transmitter 1211 is disposed above the multiple-frequency signal transmitter 1111, while the optical image sensor 1212 is disposed above the multiple-frequency signal receiver 1112. Optical transmitters 1221, 1231, 1241, 1251, and 1261 and optical image sensors 1222, 1232, 1242, 1252, and 1262 of the optical measuring units 122 to 126 are also arranged in a similar way. Thus, details in this regard will not be reiterated in the following.

The optical transmitters 1221, 1231, 1241, 1251, and 1261 of the optical measuring units 122 to 126 transmit the measuring light to the person to be measured PH. In addition, the measuring light at least covers the body areas of the person to be measured, such as the body areas BA1 to BA4 shown in FIG. 4. In addition, the optical image sensors 1212, 1222, 1232, 1242, 1252, and 1262 of the optical measuring units 122 to 126 may receive the measuring patterns MP1 to MP6 formed through reflection of the measuring light from the person to be measured. In this embodiment, the measuring light is cross-line laser light or grid laser light, and the cross-line or grid laser light of the measuring patterns MP1 to MP6 formed through reflection from the person to be measured may change in accordance with a body profile of the person to be measured PH. When the processor 130 receives the measuring patterns MP1 to MP6 from the optical image sensors 1212, 1222, 1232, 1242, 1252, and 1262 of the optical measuring units 121 to 126, the three-dimensional surface structure of the body areas of the person to be measured may be reconstructed based on curvature changes of the measuring light in the measuring patterns MP1 to MP6 at a plurality of reference points and the corresponding distance information DI1 to DI6. It should be noted that if laser beams in the measuring light are denser, a result of reconstruction is more accurate, and the person setting up the electronic device 10 may choose the cross-line laser light or grid laser light with varied densities as the measuring light based on the actual practice.

In addition, similar to the mode that the distance measuring units 111 to 116 transmit the distance measuring signals, to avoid the measuring light transmitted by the optical transmitter 1211, 1221, 1231, 1241, 1251, and 1261 from interfering each other, the processing unit 130 controls the optical transmitter 1211, 1221, 1231, 1241, 1251, and 1261 to sequentially transmit the measuring light, such that the optical image sensors 1212, 1222, 1232, 1242, 1252, and 1262 may receive the corresponding measuring patterns MP1 to MP6.

It should be noted that, in this embodiment, the measuring light may be scattered when being projected to the person to be measured, making the optical image sensor of another optical measuring unit adjacent to the optical measuring unit currently transmitting the measuring light also receive the measuring pattern generated through scattering. As shown in FIG. 6, when the optical transmitter 1261 in the optical measuring unit 126 transmits the measuring light, the optical image sensor 1252 of the optical measuring unit 125 adjacent to the optical measuring unit 126, in addition to the optical image sensor 1262 of the optical measuring unit 126, also receives a scattering pattern formed through scattering of the measuring light from the person to be measured. After the image sensor 1252 of the optical measuring unit 125 captures the scattering pattern, the scattering pattern is transmitted to the processing unit 130. In this way, when the processing unit 130 receives the measuring pattern MP6 transmitted by the optical measuring unit 126, the processing unit 130 also receives the scattering pattern from the optical measuring unit 125. The processing unit 130 may incorporate the measuring pattern MP6 and the scattering pattern in the reconstruction, so as to obtain a better three-dimensional surface structure.

In this embodiment, the electronic device 10 also includes a body weight sensor and a body fat sensor (not shown). The body weight sensor may be connected to the sensing reference surface SP and the processing unit 130. The body weight sensor may sense a body weight value through the sensing reference surface SP and transmit the body weight value to the processing unit 130. The body fat sensor may be connected to the sensing reference surface SP and the processing unit 130 and obtain a plurality of body fat values in the respective body areas of the person to be measured by, for example, transmitting a sensing current to the person to be measured PH and receiving the sensing current again through the sensing reference surface SP. When the processing unit 130 receives the body weight value and/or the body fat values corresponding to the respective body areas, the processing unit may generate an evaluation result based on the body weight value, the three-dimensional surface structure of the body areas, and the body fat values corresponding to the body areas. For example, the evaluation result may be a simplified body volume index that provides the user (i.e., the person to be measured) with a more accurate household body weight/health evaluation standard in addition to BMI or BFP.

Figure 7:
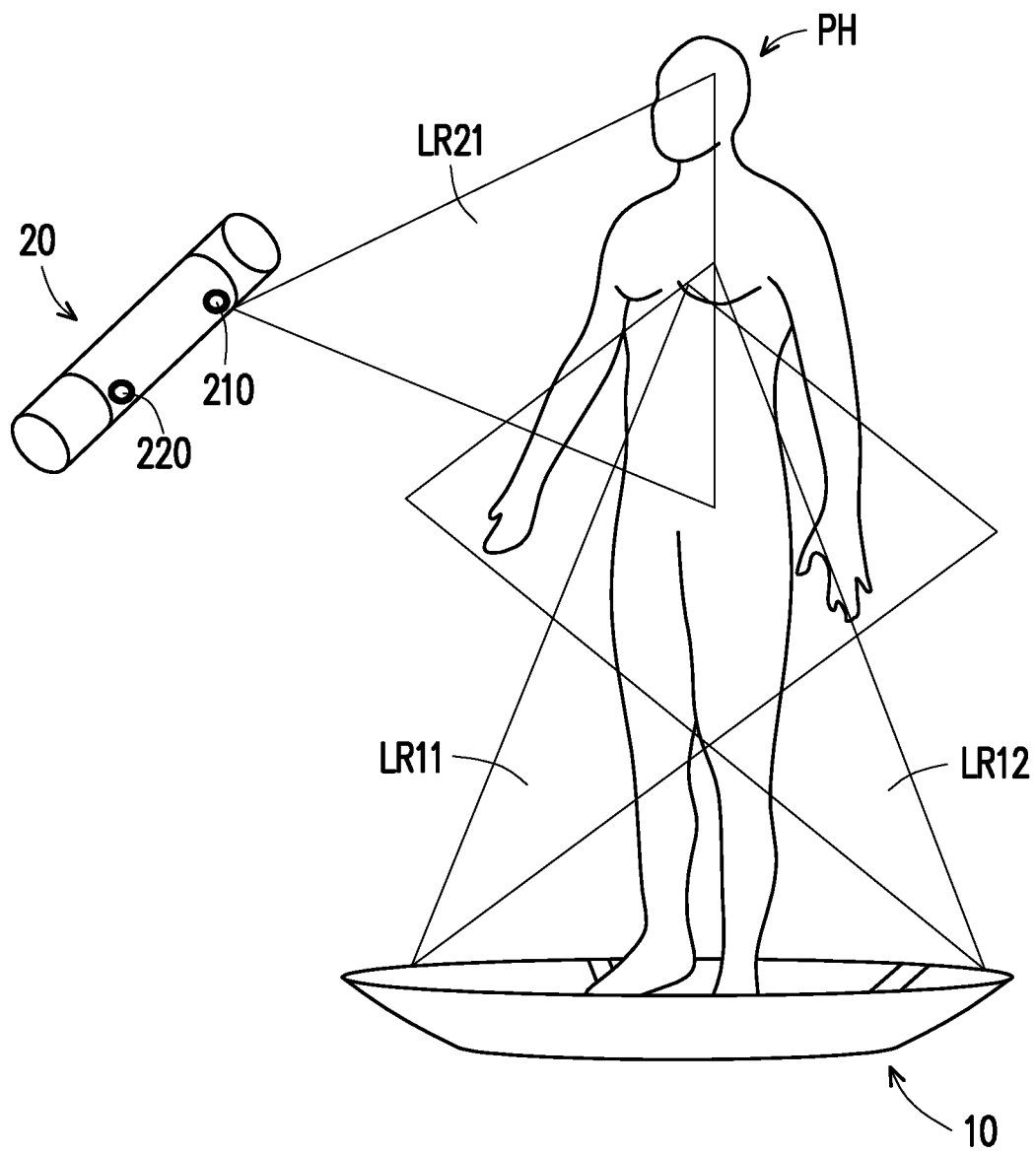
FIG. 7 is a schematic view illustrating an electronic device according to an embodiment of the invention.

FIG. 7 is a schematic view illustrating an electronic device according to an embodiment of the invention. In this embodiment, the electronic device 10 further includes an auxiliary measuring unit 20, and the auxiliary measuring unit 20 is connected to the processing unit of the human body measuring device in a wired or wireless manner. The auxiliary measuring unit 20 includes an auxiliary optical measuring unit, including an auxiliary optical transmitter 210 and an auxiliary optical image sensor 220. The auxiliary optical transmitter 210 may transmit measuring light LR21 to the person to be measured PH, and the auxiliary optical image sensor 220 may receive an auxiliary measuring pattern reflected from the person to be measured PH and transmit the auxiliary measuring pattern to the processing unit 130 of the electronic device 10.

Accordingly, the processing unit 130 is able to further add the auxiliary measuring pattern, in addition to the distance information and the measuring patterns (e.g., measuring light LR11 and LR12 shown in FIG. 7), as reference information for reconstructing the three-dimensional surface structure corresponding to the respective body areas of the person to be measured PH, so as to make the reconstruction of the three-dimensional surface structure more accurate. It should be noted that the auxiliary measuring unit 20 may be disposed together with other components, such as a handle (usually coupled to the electronic device) for measuring the body fat or a handheld electronic device such as a smart phone or a tablet computer (e.g., being connected to the processing unit 130 through an application internally operated in the handheld electronic device). However, the invention is not limited thereto.

Figure 8:
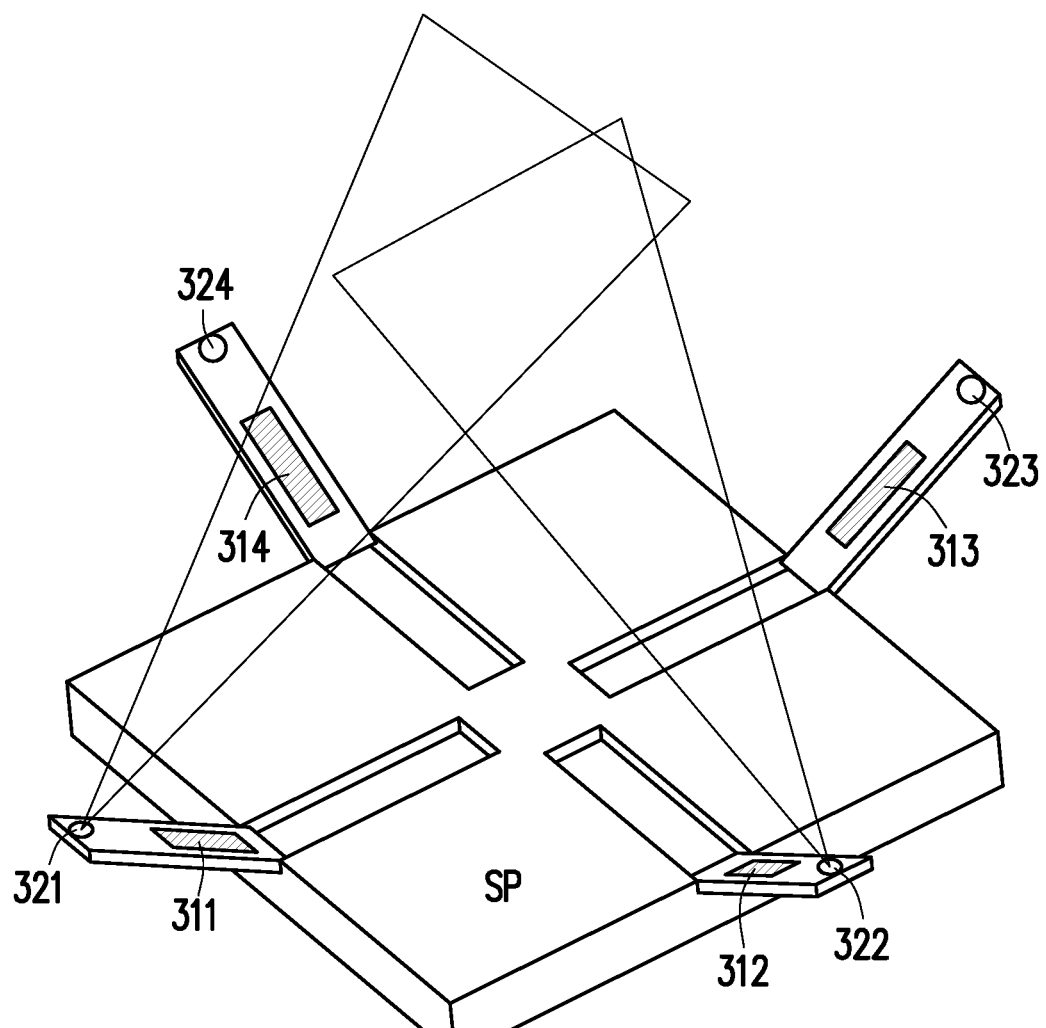
FIG. 8 is a schematic view illustrating an electronic device according to an embodiment of the invention.

FIG. 8 is a schematic view illustrating an electronic device according to an embodiment of the invention. Here, compared with the embodiment shown in FIG. 3, a device body of an electronic device 30 shown in FIG. 8 is in a square shape, and the sensing reference surface SP is also in a square shape. Also, the electronic device 30 includes four distance measuring units 311 to 314 and corresponding four optical measuring units 321 to 324. The distance measuring units 311 to 314 and the corresponding optical measuring units 321 to 324 are respectively disposed on movable structures on four sides of the reference sensing surface SP, so as to be accommodated inwardly when the user is not being measured to save the space occupied. An included angle is provided between the movable structures where the distance measuring units 311 to 314 and the optical measuring units 321 to 324 are disposed and the sensing reference surface SP, and the included angle corresponds to the included angle θ shown in FIG. 5. Thus, the person setting up the electronic device 30 or the user may make adjustment (e.g., adjusting the corresponding body areas when the height is loaded as background information) based on practical needs. Since the numbers of the distance measuring units and the optical measuring units in the electronic device 30 shown in FIG. 8 are fewer, the result of the reconstructed three-dimensional structure may not be as desirable as that of the disc-shaped embodiment shown in FIG. 3. However, the electronic device 30 shown in FIG. 8 takes up a smaller space, and the result of the three-dimensional surface structure may still be acceptable to the user.

In view of the foregoing, the invention provides the measuring device of the human body and the measuring method thereof, where a simplified way of measurement is adopted. The middle part of the body is divided into a plurality of areas, and the body shape is measured optically, and the time of flight is also used to provide the absolute reference distance. Accordingly, the body shape is reconstructed three-dimensionally. With the body weight value and the body fat value, the user may be further provided with the simplified BVI. Therefore, by using the invention, the user may be provided with BMI or BFP as well as a more accurate household body weight/health evaluation standard.

It will be apparent to those skilled in the art that various modifications and variations can be made to the structure of the present invention without departing from the scope or spirit of the invention. In view of the foregoing, it is intended that the present invention cover modifications and variations of this invention provided they fall within the scope of the following claims and their equivalents.

What is claimed is:

1. A measuring method of a human body, suitable for measuring a person to be measured standing on a sensing reference surface of a measuring device of a human body, the measuring method of the human body comprising:
   transmitting, by a plurality of distance measuring units disposed on a side edge encircling the sensing reference surface of the measuring device, a plurality of distance measuring signals to a plurality of body areas of the person to be measured, so as to obtain distance information of the body areas of the person to be measured, wherein the side edge has an included angle with respect to the sensing reference surface, and the included angle is not a right angle;
   respectively transmitting, by a plurality of optical measuring units, measuring light corresponding to the measuring signals to the person to be measured and receiving, by a plurality of optical measuring units, a plurality of measuring patterns formed through reflection of the measuring light from the person to be measured; and
   obtaining the distance information and the measuring patterns respectively corresponding the distance information, wherein a three-dimensional surface structure corresponding to the body areas of the person to be measured is calculated and reconstructed based on the respective distance information and the measuring patterns corresponding to the distance information.

2. The measuring method of the human body as claimed in claim 1, wherein the measuring method of the human body further comprises:
   sensing a weight value through the sensing reference surface; and
   generating an evaluation result based on the weight value and the three-dimensional surface structure of the body areas.

3. The measuring method of the human body as claimed in claim 2, wherein the step of generating the evaluation result based on the weight value and the three-dimensional surface structure of the body areas comprises:
   transmitting a sensing current to the person to be measured and receiving the sensing current so as to obtain a plurality of body fat values corresponding to the respective body areas of the person to be measured; and
   the step of generating the evaluation result based on the weight value and the three-dimensional surface structure of the body areas further comprises:
   generating the evaluation result based on the body weight value, the three-dimensional surface structure of the body areas, and the body fat values.

4. The measuring method of the human body as claimed in claim 1, wherein the step of obtaining the distance information to the body areas of the person to be measured comprises:
   transmitting the distance measuring signals respectively toward the body areas of the person to be measured;
   receiving the distance measuring signals through reflection from the respective body areas of the person to be measured; and
   calculating the distance information between the first distance measuring unit and the body areas based on a plurality of round-trip time values including transmitting times of respectively transmitting the distance measuring signals and receiving times of respectively receiving the distance measuring signals.

5. The measuring method of the human body as claimed in claim 4, wherein the distance measuring signals are radio frequency signals and have different central frequencies.

6. The measuring method of the human body as claimed in claim 1, wherein:
   the step of transmitting the distance measuring signals to the body areas of the person to be measured to obtain the distance information to the body areas of the person to be measured comprises:
   sequentially transmitting the distance measuring signals to the body areas of the person to be measured to sequentially obtain the distance information of the body areas of the person to be measured; and
   controlling the optical measuring units to sequentially transmit the measuring light.

7. The measuring method of the human body as claimed in claim 1, wherein:
   the step of receiving the measuring pattern formed through reflection of the measuring light from the person to be measured further comprises:
      receiving a scattering pattern formed through scattering of the measuring light from the person to be measured; and
   the step of obtaining the respective distance information and the respective measuring patterns corresponding to the respective distance information further comprises:
   obtaining the distance information and the respective distance patterns and the respective scattering patterns corresponding to the respective distance information.

8. The measuring method of the human body as claimed in claim 7, wherein before the step of reconstructing the three-dimensional surface structure corresponding to the body areas of the person to be measured, the method further comprises:
   transmitting, by an auxiliary measuring unit, an auxiliary measuring light to the person to be measured and receiving, by an auxiliary measuring unit, an auxiliary measuring pattern reflected from the person to be measured; and
   the step of reconstructing the three-dimensional surface structure corresponding to the body areas of the person to be measured comprises:
   reconstructing the three-dimensional body surface structure of the body areas of the person to be measured based on the respective distance information, the corresponding measuring patterns, and the auxiliary measuring pattern.

9. The measuring method of the human body as claimed in claim 1, wherein:
the measuring light is cross-line or grid laser light.

\* \* \* \* \*